United States Patent [19]

Collins et al.

[11] 4,105,433
[45] Aug. 8, 1978

[54] SELECTIVE HERBICIDES

[75] Inventors: David John Collins, Ascot; Ian Trevor Kay, Wokingham; John Walter Slater, Maidenhead, all of England

[73] Assignee: Imperial Chemical Industries Limited, London, England

[21] Appl. No.: 650,754

[22] Filed: Jan. 20, 1976

[30] Foreign Application Priority Data

Feb. 5, 1975 [GB] United Kingdom ............... 4885/75

[51] Int. Cl.$^2$ ............................................. A01N 9/22
[52] U.S. Cl. ............................................. 71/93; 71/82; 71/86; 71/94; 71/103; 71/113; 71/117; 544/194
[58] Field of Search ............................................. 71/93

[56] References Cited

U.S. PATENT DOCUMENTS

| | | | |
|---|---|---|---|
| 3,218,148 | 11/1965 | Knusli et al. .............. | 71/93 |
| 3,236,846 | 2/1966 | Knusli et al. .............. | 71/93 |
| 3,244,712 | 4/1966 | Knusli et al. .............. | 71/93 |
| 3,902,887 | 9/1975 | Lin .............. | 71/93 |
| 4,035,365 | 7/1977 | Kay .............. | 71/93 |

FOREIGN PATENT DOCUMENTS 806,964  5/1974  Belgium.
799,932  9/1973  Belgium.

Primary Examiner—Glennon H. Hollrah
Attorney, Agent, or Firm—Cushman, Darby & Cushman

[57] ABSTRACT

Process of controlling weed grasses by treatment with triazine-dione compounds, of the formula:

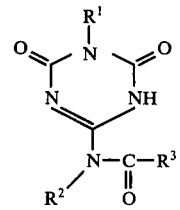

and salts thereof, wherein $R^1$ is an alkyl group of 3 to 5 carbon atoms in which the carbon atom attached to the ring nitrogen atom is a secondary or tertiary carbon atom, $R^2$ is an alkyl radical of 3 to 5 carbon atoms such that no carbon atom of the radical is linked through a linear sequence of more than two carbon atoms to the nitrogen atom to which $R^2$ is attached, and $R^3$ is methyl, ethyl, or cyclopropyl.

6 Claims, No Drawings

SELECTIVE HERBICIDES

This invention relates to processes of controlling the growth of unwanted plants, to herbicidal compositions, and to chemical compounds useful in the said processes and compositions.

In a previous patent application, there have been described herbicidal triazine-dione compounds of the formula:

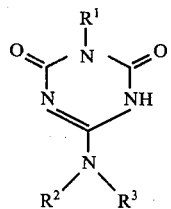

and salts thereof, wherein $R^1$ is an aliphatic radical, and either (a) $R^2$ is a carboxylic acyl radical, and $R^3$ is a hydrogen atom or an aliphatic radical, or (b) $R^2$ is a hydrogen atom or an aliphatic radical, and $R^3$ together with the group X, forms a divalent radical Z linking the nitrogen atom to which $R^3$ is attached to the nitrogen atom in the triazine ring, so as to form a second 5- or 6-membered heterocyclic ring; and X is a hydrogen atom or an aliphatic radical, or together with $R^3$ forms the divalent group Z.

As a class, these compounds were found to be less phytotoxic to maize than to many other plant species, and the above-mentioned patent application described a process of inhibiting the growth of weeds in crops of maize by applying a compound of the above formula to the crop area.

We have now discovered that within the class of compounds described in said previous patent application, there is a group of compounds which have a surprisingly different type of herbicidal activity. The members of this group of compounds are relatively more toxic towards graminaceous plant species than they are towards other plants. By graminaceous plant species we mean plants belonging to the botanical family of Gramineae, which includes all species of grasses.

Accordingly, the present invention provides a process of severely damaging or killing unwanted graminaceous plants, which comprises applying to the plants, or to the growth medium thereof, a herbicidally effective amount of a triazine-dione compound of the formula:

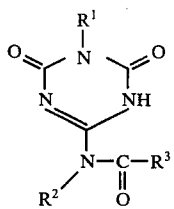

or a salt thereof, wherein $R^1$ is an alkyl radical of from 3 to 5 carbon atoms in which the carbon atom attached to the ring nitrogen atom is a secondary or tertiary carbon atom; $R^2$ is an alkyl radical of from 3 to 5 carbon atoms, the alkyl radical being such that no carbon atom of the radical is linked through a linear sequence of more than two carbon atoms to the nitrogen atom to which $R^2$ is attached; and $R^3$ is a methyl, ethyl or cyclopropyl group.

By secondary or tertiary carbon atom is meant a carbon atom which is connected to two, or to three other carbon atoms respectively. The group $R^1$ therefore, may consist, for example, of an isopropyl, 2-butyl, 3-pentyl, or t-butyl radical.

Examples of values for the group $R^2$ include n-propyl; isopropyl; isobutyl; sec butyl; t-butyl; 3-pentyl; and neopentyl. Neopentyl is a particularly preferred group. The ring NH group in the compounds of the last foregoing formula is acidic and the compounds can therefore form salts with bases.

Salts of compounds used in the invention include, for example, alkali metal salts, for example lithium, sodium, and potassium salts; and alkaline earth metal salts, for example salts of calcium and magnesium. Further examples of salts include salts formed from ammonia, and from primary, secondary, and tertiary amines, for example primary, secondary, and tertiary aliphatic amines. Examples of aliphatic amines include isopropylamine, dimethylamine, triethylamine and Armeen 2C. Armeen 2C is a Trade Mark for a commercially available mixture of secondary amines derived from coconut oil, in which the aliphatic radicals are principally dodecyl and tetradecyl radicals.

Particular examples of compounds useful in the invention are listed in Table I below.

TABLE I

| COMPOUND NO | $R^1$ | $R^2$ | $R^3$ | MELTING POINT ° C |
|---|---|---|---|---|
| 1 | iso $C_3H_7$ | n $C_3H_7$ | $CH_3$ | 74–75 |
| 2 | iso $C_3H_7$ | sec $C_4H_9$ | $CH_3$ | 71–73 |
| 3 | iso $C_3H_7$ | iso $C_4H_9$ | $CH_3$ | 83–85 |
| 4 | iso $C_3H_7$ | n $C_3H_7$ | $C_2H_5$ | 104–105 |
| 5 | sec $C_4H_9$ | n $C_3H_7$ | $CH_3$ | 79–83 |
| 6 | iso $C_3H_7$ | neo $C_5H_{11}$ | $CH_3$ | 136–138 |
| 7 | t $C_4H_9$ | n $C_3H_7$ | $CH_3$ | 89–90 |
| 8 | sec $C_4H_9$ | neo $C_5H_{11}$ | $CH_3$ | 74–77 |
| 9 | iso $C_3H_7$ | neo $C_5H_{11}$ | $C_2H_5$ | 123–125 |
| 10 | iso $C_3H_7$ | iso $C_3H_7$ | $CH_3$ | 100–101 |
| 11 | t-$C_4H_9$ | neo $C_5H_{11}$ | $CH_3$ | Glass |
| 12 | iso $C_3H_7$ | neo $C_5H_{11}$ | cyclopropyl | 57–59 |

The compounds used in the process of the invention may be applied to severely damage or kill unwanted graminaceous plants both in the situation when the unwanted graminaceous plants are growing in a non-graminaceous crop, and when they are growing where no crop is present.

Accordingly, the invention further provides a process of selectively controlling the growth of graminaceous weeds in a non-graminaceous crop, which comprises applying to the crop area a triazine-dione compound of the last foregoing formula, in an amount sufficient to control the growth of the graminaceous weeds, but insufficient to substantially damage the crop.

The compounds used in the process of the invention are effective both by application directly to the foliage of growing plants ("post-emergence application") and by application to the soil to prevent the emergence of plants from seeds present in the soil ("pre-emergence application"). When applying the compounds to soil, it may sometimes be advantageous to follow up the application of the compound by cultivating the soil to a shallow depth (e.g. 3-5 centimeters) in order to incorporate the compound into the soil. Generally speaking the compounds are more effective when applied post-emergence than by pre-emergence application.

The amount of the triazine-dione compound applied in the process of the invention will depend upon a number of factors, such as the identity of the particular graminaceous plants to be controlled, and the particular compound chosen for use. The determination of appropriate rates of application is a routine matter to one skilled in the art, but by way of general guidance, application rates typically lie in the range from 0.25 to 10 kilograms per hectare, and usually within the range 0.5 to 5.0 kilograms per hectare. Generally speaking, the triazine-dione compounds are more effective against annual grasses than against perennial grasses.

Examples of non-graminaceous crops include, for example, leguminous crops, for example ground-nuts, beans, peas, soyabean and lucerne. Further examples of non-graminaceous crops include cotton, sugar beet, rape, linseed, sunflower, safflower, onions, and cruciferous crops, for example lettuce and cabbage. The triazine-dione compounds may also be used to control cereal plants appearing as weeds in non-graminaceous crops.

The selective toxicity of the compounds towards grass species is surprising when their herbicidal effects are compared with those of acylaminotriazinedione compounds which, while falling outside the scope of the present invention, are closely related. Results of herbicidal tests conducted with examples of such closely related acylaminotriazinedione compounds are given in Example 1, and it will be seen that they tend to be broad-spectrum herbicides, that is to say generally toxic to all the plant species employed in the tests. They do have some selectivity but this is shown as a less toxic effect on the graminaceous species, especially maize. Thus the selectivity of these compounds is the direct opposite of the selectivity of the compounds of the present invention.

The applicants do not wish to be bound by any theory as to the mode of action of the compounds used in the invention as selective herbicides. However, it may be noted that the de-acylated compounds of formula (II)

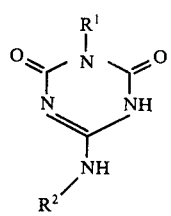

(II)

have little or no activity at rates of application which in the case of the compounds of the invention cause severe damage or complete kill, as illustrated in Example 1. In biochemical experiments, it has been found that when applied to plants, the concentration of triazine-dione compound subsequently found in the tissues of a resistant plant (sugar-beet) decreases much more quickly than the concentration in a susceptible plant (*Digitaria sanguinalis*). It therefore appears that the selective herbicidal activity of the compounds used in the invention may result from the ability of the resistant plants to convert the compounds to the non-phytotoxic compounds of formula (II), while the susceptible graminaceous plants are relatively less efficient in performing this conversion.

If desired, the triazine-dione compound may be applied in admixture with one or more other herbicides. The admixed herbicide may, for example, be one which is capable of controlling broad leaved weeds, so that by use of the mixture a wide spectrum of weed control may be achieved. When the triazine-dione compound is being applied to a non-graminaceous crop in order to selectively control the growth of weeds, any additional herbicide applied in admixture with the triazine-dione compound must be one which is itself substantially non-phytotoxic towards the crop. The skilled worker in the art of weed control will be aware of the herbicides which are known to be suitable for selective weed control in particular crops, but by way of examples, herbicides suitable for admixture with the triazine-dione compounds used in the present invention are described below for several non-graminaceous crops.

Thus, when used for controlling weeds in leguminous crops, the triazine-dione compounds may be mixed, for example with dinoseb, bentazon, chloramben, metribuzin, 2,4-DB, MCPB or chloroxuron. For use in cotton, the triazine-dione compounds may be mixed for example with fluometuron, diuron, noruron, methazole, or prometryne. When used in sugar-beet, the triazine-dione compounds may be mixed for example with phenmedipham, desmedipham, pyrazon, lenacil, benzadox, nortram, or metanitron. When used in oil-seed rape, the triazine-dione compounds may be mixed with, for example, aziprotryne, dicamba, or benazolin.

As noted above, the triazine-dione compounds may be applied to control grass weeds in areas where no crop is being grown; for example, to control grass weeds growing in the stubble remaining after a cereal crop has been harvested. If desired, the triazine-dione compounds may be applied in admixture with additional herbicides. Examples of such herbicides include salts of paraquat (1,1'-dimethyl-4,4'-bipyridylium cation), for example paraquat dichloride or paraquat dimethylsulphate. Other examples of herbicides which may be admixed include N-phosphonomethylglycine (glyphosate), 2,4-dichlorophenoxyacetic acid (2,4-D) and 2,2-dichloropropionic acid (dalapon). Mixtures with paraquat have the advantage that the above ground parts of the plants are more rapidly killed than when the triazine-dione compound is used alone. The mixtures have also been found to give a greater herbicidal effect than would have been predicted by calculation from the observed effects of the two herbicides applied separately.

In mixtures of the triazine-dione compounds with other herbicides, the proportions of the active ingredients may be varied at the choice of the user of the mixture, depending upon the purpose for which the mixture is to be employed. In the case of mixtures of the triazine-dione compounds with paraquat, a preferred range of proportions is from one to four parts of triazine-dione compound to one part of paraquat.

The triazine-dione compounds may also be used in admixture with known conventional additives or adjuvants for improving the effectiveness of herbicides. Thus, in post-emergence tests, improved herbicidal effects have been obtained by applying the triazine-dione compound in admixture with for example, tributylphosphate, ammonium sulphate, and dimethylsulphoxide.

The triazine-dione compounds and their mixtures with other herbicides are preferably applied in the form of a composition, which comprises the active ingredient or ingredients mixed with a carrier comprising a solid or liquid diluent. Preferably the composition also contains a surface-active agent.

Compositions according to the invention include both dilute compositions, which are ready for immediate use, and concentrated compositions, which require to be diluted before use, usually with water. Preferably the compositions contain from 0.1% to 90% by weight of the triazine derivative used as active ingredient. Dilute compositions ready for use preferably contain from 0.01 to 2% of active ingredient, while concentrated compounds may contain from 10 to 90% of active ingredient, although from 20 to 70% is usually preferred.

Solid compositions may be in the form of a powder, in which the active ingredient is mixed with a powdered solid diluent. Suitable solid diluents include for example, Fuller's earth, powdered kaolin, gypsum, chalk and keiselguhr. Such solid compositions may be applied as foliar dusts.

Liquid compositions may comprise a solution or dispersion of an active ingredient in water optionally containing a surface-active agent, or may comprise a solution or dispersion of an active ingredient in a water-immiscible organic solvent. In use, the concentrated liquid compositions may be dissolved or dispersed in water to provide a dilute composition for spraying.

Examples of surface-active agents which may be used in the compositions of the invention include the products of condensation of ethylene oxide with the following substances: alkyl substituted phenols such as octyl phenol and nonylphenol; sorbitan monolaurate; oleyl alcohol and propylene oxide polymer. A particular example of such a condensation product is the condensate of p-nonylphenol with from 7 to 8 molar proportions of ethylene oxide sold under the name of "Lissapol" ("Lissapol" is a Trade Mark). Other examples of surface-active agents include calcium dodecylbenzenesulphonate, and calcium, sodium, and ammonium lignosulphonates.

Particular examples of compositions according to the invention include liquid compositions in which the active ingredient is dissolved in a water-immiscible organic solvent, for example methylcyclohexanone, together with one or more surface-active agents. A typical liquid composition has the following contents:

| Component | Amount (grams per liter) |
|---|---|
| Compound no. 6 of Table 1 | 100 |
| Span 80 | 50 |
| Tween 80 | 50 |
| Sextone B (methylcyclohexanone) | to 1 liter |

Solid compositions include water-soluble powders, for example a water-soluble powder comprising the sodium salt of compound no. 6 of Table I.

In another aspect, the invention provides herbicidal triazine-dione compounds, having the formula:

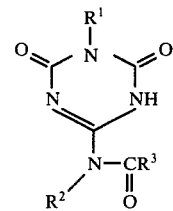

and salts thereof, wherein $R^1$ is an alkyl radical of from 3 to 5 carbon atoms in which the carbon atom attached to the ring nitrogen atom is a secondary or tertiary carbon atom; $R^2$ is an alkyl radical of from 3 to 5 carbon atoms, the alkyl radical being such that no carbon atom of the radical is linked through a linear sequence of more than two carbon atoms to the nitrogen atom to which $R^2$ is attached; and $R^3$ is a methyl, ethyl, or cyclopropyl group, provided that when $R^3$ is methyl and $R^1$ is isopropyl, $R^2$ is not a n-propyl or isopropyl group. Preferred compounds include those in which (a) $R^1$ is isopropyl, $R^2$ is neopentyl and $R^3$ is methyl and (b) $R^1$ is 2-butyl, $R^2$ is neopentyl and $R^3$ is methyl.

The compounds of the invention may be prepared by acylating an aminotriazine compound of the following formula (II) with acetic or propionic anhydride or with acetyl or propionyl chloride, or with cyclopropane carboxylic acid anhydride or chloride, as in the following scheme:

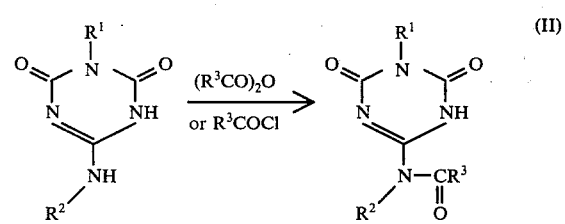

The reaction may be carried out at a range of temperatures, for example, at room temperature or above. Conveniently, the reaction may be accelerated by heating, for example at the boiling point of acetic anhydride or propionic anhydride. It is preferred to carry out the reaction in a diluent or solvent for the reactants. Conveniently, the diluent may be an excess of acetic or propionic anhydride.

The reaction may be carried out by heating the compound in an excess of the acetic or propionic anhydride and distilling off the acetic or propionic acid as it is formed.

The aminotriazine derivatives (II) used as starting materials for preparing compounds according to the invention are representatives of a known type of compounds, although those used as intermediates for the compounds of Table I are believed to be novel in themselves. They may be prepared by the application of known methods. Thus they may be prepared, for example, by the method outlined in reaction scheme A below, as described in Belgian Patent 806,964.

Scheme A (II)

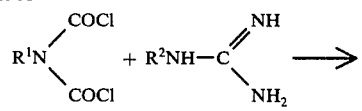

In scheme A, $R^1$ and $R^2$ have the meanings previously assigned to them in this specification. According to scheme A, a bis-chlorocarbonyl amine is reacted with a guanidine. The bis-chlorocarbonyl amines and the guanidines used in the preparation of the triazine-diones (II) are known compounds, or can be prepared by methods analogous to those used for known compounds.

In an alternative method the aminotriazine derivatives (II) may be obtained by reaction of an amine $R^2 NH_2$ with a methylmercaptotriazine of formula (III) as shown in scheme B below:

Scheme B

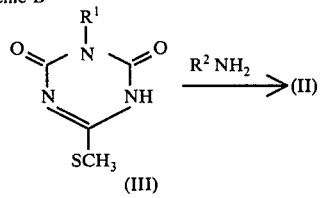

The amine $R^2 NH_2$ is preferably used in the form of an acid addition salt with a lower aliphatic carboxylic acid. Examples of such salts include the acetate and the propionate salts of the amine $R^2 NH_2$. The reaction may conveniently be carried out by heating the methylthiotriazine (III) with the amine salt either in the presence or the absence of a diluent. The preparation of methylthiotriazine derivatives of type (III) is known, having been described, for example, in Belgian Pat. No. 799932. A further alternative method for the preparation of the aminotriazine derivatives (II) is set out in scheme C below:

Scheme C

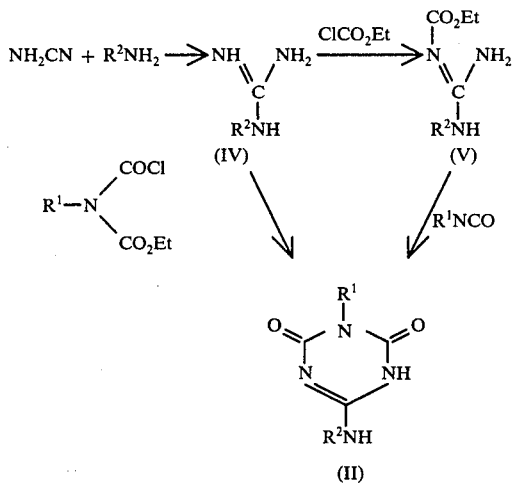

In Scheme C, an amine $R^2NH_2$ is reacted with cyanamide to give a substituted guanidine (IV). This may then be reacted with the acid chloride derivative

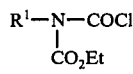

to give the required aminotriazine derivative directly, or alternatively may be reacted with ethyl chloroformate to give the carbamate derivative (V). The latter may then be reacted with an isocyanate $R^1NCO$ to give the aminotriazine derivative (II).

The invention is illustrated by the following Examples.

EXAMPLE 1

This Example illustrates the herbicidal properties of compounds according to the invention.

Each compound (0.12 g) was mixed with 5 ml of an emulsion prepared by diluting 100 ml of a solution containing 21.8 grams per liter of Span 80 and 78.2 grams per liter of Tween 20 in methylcyclohexanone to 500 ml with water. Span 80 is a Trade Mark for a surface-active agent comprising sorbitan monolaurate. Tween 20 is a Trade Mark for a surface-active agent comprising a condensate of sorbitan monolaurate with 20 molar proportions of ethylene oxide. The mixture of the compound and the emulsion was shaken with glass beads and then diluted to 12 ml with water.

The spray composition so prepared was sprayed onto young pot plants (post-emergence test) of the species named in Table II below, at a rate equivalent to 1000 liters per hectare (10 kilograms of triazine derivative per hectare). Damage to plants was assessed 14 days after spraying by comparison with untreated plants, on a scale of 0 to 3 where 0 is 0 to 25% damage and 3 represents 75 to 100% kill. In a test for pre-emergence herbicidal activity, seeds of the test species were placed on the surface of fibre trays of soil and were sprayed with the compositions at the rate of 1000 liters per hectare. The seeds were then covered with further soil. Fourteen days after spraying, the seedlings in the sprayed fibre trays were compared with the seedlings in unsprayed control trays, the damage being assessed on the same scale of 0 to 3. The results are given in Table II below.

TABLE II

| Compound No. | Time of Application | Test Plants | | | | | |
|---|---|---|---|---|---|---|---|
| | | Le | To | Cl | Wh | Dg | Pr |
| 1 | Pre | 0 | 0 | 0 | 0 | 0 | 1 |
| | Post | 0 | 1 | 1 | 3 | 3 | 0 |
| 2 | Pre | 0 | 0 | 0 | 0 | 1 | 0 |
| | Post | 0 | 1 | 2 | 3 | 3 | 0 |
| 3 | Pre | 0 | 0 | 0 | 1 | 2 | 3 |
| | Post | 1 | 0 | 2 | 3 | 3 | 2 |
| 4 | Pre | 0 | 0 | 0 | 0 | 1 | 3 |
| | Post | 0 | 0 | 2 | 1 | 3 | 2 |
| 5 | Pre | 0 | 1 | 0 | 3 | 3 | 1 |
| | Post | 0 | 0 | 1 | 1 | 3 | 3 |

The names of the test species were as follows:
Le: Lettuce
To: Tomato
Cl: Red Clover
Wh: Wheat
Dg: *Digitaria sanguinalis*
Pr: *Lolium perenne*

By way of comparison, the results of post-emergence tests carried out as described above on acylaminotriazinedione compounds closely related to compounds of the present invention are collected in Table IV.

The structures of these compounds are given in Table III below:

TABLE III

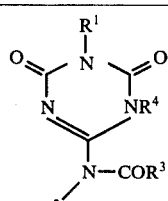

Structures of Comparison Compounds

| | R¹ | R² | R³ | R⁴ |
|---|---|---|---|---|
| A | iso C$_3$H$_7$ | CH$_3$ | CH$_3$ | H |
| B | iso C$_3$H$_7$ | C$_2$H$_5$ | CH$_3$ | H |
| C | iso C$_3$H$_7$ | CH$_3$ | CH$_3$ | CH$_3$ |
| D | iso C$_3$H$_7$ | CH$_3$ | nC$_3$H$_7$ | H |
| E | cyclo hexyl | CH$_3$ | CH$_3$ | H |

TABLE IV

Test Results with Comparison Compounds

| Compound | Le | To | Cl | Wh | Dg | Pr |
|---|---|---|---|---|---|---|
| A | 3 | 3 | 3 | 2 | 3 | 3 |
| B | 3 | 3 | 3 | 0 | 3 | 3 |
| C | 3 | 3 | 3 | 0 | 2 | 0 |
| D | 3 | 3 | 3 | 2 | 3 | 2 |
| E | 3 | 3 | 3 | 1 | 3 | 2 |

It will be seen from Table IV that compounds A to E have a different spectrum of herbicidal activity from that of the compounds of the invention. Compounds A to E damaged both grass species and broadleaved species, but were relatively less phytotoxic towards grasses, in contrast to compounds 1 to 5, which, as shown in Table II, were more damaging to grasses than to broadleaved plants.

In an additional test carried out for purposes of comparison, aminotriazinedione derivatives of formula (II) were examined. The structures of these compounds, referring to formula (II), were as follows:

| Compound | R¹ | R² |
|---|---|---|
| F | iso C$_3$H$_7$ | n C$_3$H$_7$ |
| G | sec C$_4$H$_9$ | n C$_3$H$_7$ |
| H | iso C$_3$H$_7$ | neo pentyl |

The results of the test are given in Table V below:

TABLE V

| COMPOUND | TIME OF APPLICATION | Le | To | Cl | Wh | Dg | Pr |
|---|---|---|---|---|---|---|---|
| F | Pre | 0 | 0 | 0 | 0 | 0 | 0 |
|   | Post | 0 | 0 | 0 | 0 | 0 | 0 |
| G | Pre | 0 | 0 | 0 | 0 | 0 | 0 |
|   | Post | 0 | 0 | 1 | 0 | 1 | 0 |
| H | Pre | 0 | 0 | 0 | 0 | 0 | 0 |
|   | Post | 0 | 0 | 0 | 0 | 0 | 0 |

It will be seen from Table V, that compounds F, G and H are without herbicidal activity at the same rate (10 kilograms per hectare) at which compounds of the invention have high levels of herbicidal activity. Compound F is the intermediate compound from which compounds 1 and 4 of Table I were prepared by acylation. Compound G is the intermediate from which compound No. 5 of Table I was prepared. Compound H is the intermediate from which compound No. 6, 9 and 12 of Table I were prepared.

EXAMPLE 2

This Example further illustrates the herbicidal properties of compounds according to the invention. Tests were carried out as described in Example 1, but using a wider range of test species and various rates of application. Each compound was formulated for test by mixing an appropriate amount with 5 ml of an emulsion prepared by diluting 160 ml of a solution containing 21.8 g per liter of Span 80 and 78.2 g per liter of Tween 20 in methylcyclohexanone to 500 ml with water. The 5 ml of emulsion containing the test compound was then diluted to 40 ml with water and sprayed on to the range of test plants. The pre-emergence test was carried out in a slightly different way from the test described in Example 1. The seeds of the plants were sown in a shallow slit formed in the soil, and the surface levelled and sprayed. Fresh soil was then spread thinly over the sprayed surface. The results of tests carried out in this way are collected in Tables VI, VII and VIII and are expressed in terms of a number on the scale 0 to 9 where 0 is 0 to 11% damage and 9 is complete kill. A dash (-) means that no test was carried out.

TABLE VI

| COMPOUND No | RATE OF APPLICATION kg/ha | TIME OF APPLICATION | Mz | Rc | Sg | Sy | Gn | Ct | Ei | Ec | St | Dg | Po | Am |
|---|---|---|---|---|---|---|---|---|---|---|---|---|---|---|
| 1 | 2.0 | Pre | 2 | 3 | 5 | 1 | 0 | 0 | 8 | 6 | 8 | 0 | 0 | 0 |
|   | 2.0 | Post | 6 | 7 | 9 | 3 | 0 | 1 | 9 | 9 | 9 | 9 | 3 | 3 |
| 2 | 3.0 | Pre | 1 | 5 | 2 | 0 | 1 | 0 | 9 | 0 | 8 | 1 | 1 | 1 |
|   | 3.0 | Post | 4 | 8 | 8 | 3 | 1 | 1 | 9 | 9 | 9 | 9 | 1 | 0 |
| 3 | 2.0 | Pre | 0 | 3 | 8 | 0 | 0 | 0 | 9 | 8 | 8 | 3 | 2 | 0 |
|   | 2.0 | Post | 4 | 8 | 9 | 2 | 1 | 1 | 9 | 9 | 9 | 7 | 1 | 2 |
| 4 | 2.0 | Pre | 0 | 2 | 2 | 0 | 0 | 0 | 9 | 3 | 8 | 7 | 0 | 0 |
|   | 2.0 | Post | 2 | 3 | 7 | 1 | 2 | 1 | 9 | 7 | 9 | 8 | 0 | 2 |
| 6 | 4.0 | Pre | 2 | 9 | 7 | 0 | 0 | 0 | 9 | 9 | 9 | 3 | 0 | 0 |
|   | 4.0 | Post | 7 | 9 | 9 | 2 | 1 | 4 | 9 | — | 9 | 9 | 9 | 1 |
| 10 | 4.0 | Pre | 0 | 7 | 6 | 0 | 0 | 0 | 8 | 8 | 8 | 0 | 0 | 0 |
|    | 4.0 | Post | 8 | 9 | 9 | 4 | — | 1 | 9 | 9 | 9 | 9 | 9 | 6 |

The names of the test plants in Table VI are as follows:
Mz: Maize
Rc: Rice
Sg: Sorghum
Sy: Soya bean
Gn: Ground nut
Ct: Cotton
Ei: *Eleusine indica*
Ec: *Echinochloa crus-galli*
St: *Setaria viridis*
Dg: *Digitaria sanguinalis*
Po: *Portulaca oleracae*
Am: *Amaranthus retroflexus*

It will be seen from Table VI that compounds 1 to 4, 6 and 10 show pronounced selectivity in their herbicidal action, being severely damaging towards the grass species, for example, *Eleusine indica* and *Setaria viridis*, while being relatively non-toxic towards, for example, ground nut and cotton.

The results of further tests are given in Tables VII and VIII below.

To: Tomato
Al: *Alopecurus myosuroides*
Sm: *Stellaria media*
Ca: *Chenopodium album*
Pl: *Polygonum persicaria*
Sn: *Senecio vulgaris*
Sp: *Sinapis alba*

TABLE VII

| COMPOUND NO | APPLICATION RATE, kg/ha | PRE- OR POST- EMERGENCE | TEST PLANTS | | | | | | | | | |
|---|---|---|---|---|---|---|---|---|---|---|---|---|
| | | | Ww | Br | Pe | Fb | Av | Al | Sm | Ca | Pi | Tm |
| 1 | 4.0 | Pre | 3 | — | 0 | 1 | 9 | 8 | 3 | 3 | 0 | — |
| | 4.0 | Post | 9 | 9 | 1 | 0 | 9 | 9 | 0.413 | 0 | 0 | |
| 2 | 4.0 | Pre | 7 | 7 | 0 | 0 | 6 | 2 | 0 | 0 | 0 | 0 |
| | 4.0 | Post | 7 | 9 | 0 | 0 | 9 | 9 | 1 | — | 4 | 0 |
| 3 | 4.0 | Pre | 7 | — | 0 | 1 | 5 | 9 | 4 | 2 | 0 | 0 |
| | 4.0 | Post | 9 | 9 | 0 | 0 | 9 | 9 | 2 | 3 | 0 | 0 |
| 4 | 4.0 | Pre | 0 | — | 1 | 2 | 2 | 4 | 4 | 3 | 1 | 6 |
| | 4.0 | Post | 5 | 8 | 1 | 1 | 9 | 8 | 1 | 6 | 0 | 0 |
| 6 | 2.0 | Pre | 9 | 9 | 0 | 0 | 9 | 9 | 0 | 0 | 0 | 0 |
| | 2.0 | Post | 9 | 9 | 2 | 1 | 9 | 9 | 3 | 1 | 2 | 0 |
| 10 | 4.0 | Pre | 8 | 7 | 0 | 0 | 7 | 3 | 0 | 0 | 0 | 0 |
| | 4.0 | Post | 9 | 9 | 1 | 0 | 9 | 9 | 2 | — | 3 | 2 |

The names of the test plants were as follows:
Ww: Winter wheat
Br: Barley
Pe: Pea
Fb: Field bean
Av: *Avena fatua*
Al: *Alopecurus myosuroides*
Sm: *Stellaria media*
Ca: *Chenopodium album*
Pi: *Polygonum aviculare*
Tm: *Tripleurospermum maritinum*

TABLE VIII

| COMPOUND NO | APPLICATION RATE kg/hg | PRE- OR POST- EMERGENCE | TEST PLANTS | | | | | | | |
|---|---|---|---|---|---|---|---|---|---|---|
| | | | Sr | To | Al | Sm | Ca | Pl | Sn | Sp |
| 1 | 2.0 | Pre | 0 | 1 | 7 | 0 | 1 | 0 | 0 | 0 |
| 1 | 2.0 | Post | 0 | 0 | 9 | 0 | 0 | 0 | 0 | 0 |
| 2 | 4.0 | Pre | 0 | 0 | 3 | 2 | 0 | 0 | 5 | 1 |
| 2 | 4.0 | Post | 0 | 1 | 9 | 6 | 6 | 0 | 3 | 8 |
| 6 | 1.0 | Pre | 0 | 0 | 9 | 0 | 1 | 5 | 3 | 0 |
| 6 | 1.0 | Post | 1 | 2 | 9 | 0 | 1 | 0 | 0 | 1 |
| 10 | 4.0 | Pre | 0 | 0 | 4 | 2 | 0 | — | 0 | 1 |
| 10 | 4.0 | Post | 1 | 2 | 9 | 6 | 8 | 1 | 2 | 9 |

The names of the test plants are as follows:
Sr: Sunflower

EXAMPLE 3

This Example illustrates the herbicidal activity of further compounds used in the invention. The compounds were formulated and tested as in Example 2. The rate of application was 5 kilograms per hectare and the results are given in Table IX below:

TABLE IX

| COMPOUND NO | PRE- OR POST- EMERGENCE | TEST PLANTS | | | | | | | | | |
|---|---|---|---|---|---|---|---|---|---|---|---|
| | | Sn | Ip | Am | Pi | Ca | Po | Ot | Dg | Ei | Pu |
| 5 | Pre | 0 | 1 | 0 | 0 | 0 | 0 | 1 | 1 | 5 | 0 |
| | Post | 2 | 2 | 0 | 0 | 3 | 1 | — | 4 | 5 | 2 |
| 7 | Pre | 0 | 0 | 0 | 0 | 0 | 0 | 1 | 1 | 4 | 0 |
| | Post | 2 | 1 | 4 | 2 | 4 | 2 | 0 | 3 | 4 | 4 |
| 9 | Pre | 1 | 0 | 0 | 0 | 0 | 0 | 3 | 0 | — | 1 |
| | Post | 0 | 0 | 0 | 3 | 0 | 1 | 4 | 1 | — | 5 |

EXAMPLE 4

This Example illustrates the herbicidal effects of compound no. 8 of Table I. Herbicidal tests were carried out as described in Example 2, but using various different groups of test plants. The application rate was 4 kilograms per hectare in each test. The results are given in Tables X to XII below:

TABLE X

| PRE- OR POST- EMERGENCE APPLICATION | TEST PLANTS | | | | | | | | | | | | | |
|---|---|---|---|---|---|---|---|---|---|---|---|---|---|---|
| | Ww | Br | Pe | Rp | Sb | Lt | Av | Al | Bt | Ag | Sm | Ca | Pi | Ma | Sp |
| Pre | 8 | 9 | 0 | 0 | 0 | 0 | 8 | 9 | 9 | 9 | 0 | 0 | 1 | 0 |
| Post | 9 | 9 | 1 | 2 | 2 | 0 | 9 | 9 | 9 | 9 | 1 | 2 | 3 | 1 | 2 |

TABLE XI

| PRE- OR POST-EMERGENCE APPLICATION | TEST PLANTS | | | | | | | | | | | | | |
|---|---|---|---|---|---|---|---|---|---|---|---|---|---|---|
| | Mz | Sy | Gn | Ct | To | Po | Am | Ip | Dt | Ab | Se | Co | Si | Ds | Xz |
| Pre | 1 | 0 | 0 | 0 | 0 | 0 | 0 | 0 | 1 | 1 | 2 | 1 | 0 | 0 | 1 |
| Post | 8 | 2 | 0 | 2 | 4 | 1 | 5 | 3 | 1 | 0 | 0 | 1 | 0 | 1 | 1 |

TABLE XII

| Pre- or Post-Emergence Application | TEST PLANTS | | | | | | | | | | |
|---|---|---|---|---|---|---|---|---|---|---|---|
| | Ct | Rc | Sg | Ei | Ec | Dg | St | Sf | Sh | Cn | Am |
| Pre | 1 | 9 | 9 | 9 | 8 | 9 | 9 | 8 | — | 1 | 1 |
| Post | 1 | 9 | 9 | 9 | 9 | 9 | 9 | 9 | 9 | 3 | 3 |

The names of the test plants not used in previous examples are as follows:
Rp: Rape
Lt: Lettuce
Bt: *Bromus tectorum*
Ag: *Agropyron repens*
Ip: *Ipomoea purpurea*
Dt: *Desmodium tortuosum*
Cp: *Cyperus rotundus*
Sh: *Sorghum halepense*
Ab: *Abutilon theophrasti*
Se: *Sesbania exaltata*
Co: *Cassia obtusifolia*
Si: *Sida spinosa*
Ds: *Datura stramonium*
Xa: *Xanthium pensylvanicum*
Sf: *Setaria faberii*

EXAMPLE 5

This Example illustrates the selective herbicidal activity of compound no. 6 of Table I. For comparison, the results of tests carried out with comparison compound D are included. The compounds were tested according to the procedures described in Example I, but using a different range of test plants and rates of application. Damage to the plants was assessed two weeks after application, on a 0 to 5 scale where 5 is complete kill and 0 is 0 to 20% damage. The results are given in Table XIII.

TABLE XIII

| COMPOUND NO | TIME OF APPLICATION | RATE OF APPLICATION KG/HA | TEST PLANTS | | | | | | | | | | | | | | | |
|---|---|---|---|---|---|---|---|---|---|---|---|---|---|---|---|---|---|---|
| | | | Sb | Rp | Ct | P | Sn | Ip | Am | Pa | Ca | Po | Mz | Ba | Rc | Ot | Dg | El | Pn |
| 6 | Pre | 5 | 0 | 0 | 1 | 0 | 0 | 0 | 0 | 0 | 0 | 0 | 5 | 5 | 5 | 5 | 2 | 5 | 5 |
| 6 | Pre | 1 | 0 | 0 | 0 | 0 | 0 | 0 | 0 | 0 | 0 | 2 | 0 | 5 | 5 | 5 | 0 | 5 | 4 |
| 6 | Post | 5 | 0 | 0 | 0 | 0 | 0 | 0 | 0 | 1 | 0 | 0 | 3 | — | 5 | 5 | 5 | 5 | 5 |
| 6 | Post | 1 | 0 | 0 | 0 | 0 | 0 | 0 | 1 | 0 | 0 | 0 | 0 | — | 4 | 5 | 5 | 5 | 4 |
| D | Pre | 5 | 1 | 0 | 0 | 0 | 5 | 0 | 2 | 3 | 0 | 3 | 0 | 0 | 0 | 0 | 0 | 0 | 0 |
| D | Pre | 1 | 0 | 0 | 0 | 0 | 5 | 0 | 0 | 3 | 0 | 0 | 1 | 0 | 0 | 0 | 0 | 0 | 0 |
| D | Post | 5 | 5 | 5 | 5 | 3 | 5 | 5 | 5 | 5 | 5 | 5 | 1 | 4 | 4 | 4 | 5 | 5 | 5 |
| D | Post | 1 | 5 | 5 | 5 | 1 | 5 | 5 | 5 | 5 | 5 | 5 | 0 | 4 | 3 | 3 | 4 | 5 | 5 |

It will be seen that there is a striking contrast between the pattern of selectivity of compound 6 and that of compound D, compound 6 being highly damaging and in most cases lethal towards the grass species. Compound D is less selective, and its herbicidal activity is relatively greater on broadleaved species than on grasses.

EXAMPLE 6

This Example illustrates the preparation of compound no. 1 of Table I.

A mixture of 1-isopropyl-4-propylamino-1,3,5-triazine-2,6-dione (5.0 g) having a melting point of 107°–108° C and acetic anhydride (25 ml) was heated under reflux for 3 hours. The excess of acetic anhydride was removed in a vacuum and the residual oil triturated with n-hexane to give a solid. Re-crystallisation from a mixture of ether and n-hexane gave compound no. 1 of Table I having a melting point of 74°–75° C.

EXAMPLE 7

Following a procedure similar to that described in Example 6, the remaining compounds of Table I were prepared, using the appropriate amino-triazinedione compound and acid anhydride. The melting points of the aminotriazinediones used as starting materials are tabulated below (Table XIV):

TABLE XIV $$\text{structure with } R^1, R^2$$

| $R^1$ | $R^2$ | MELTING POINT °C |
|---|---|---|
| iso $C_3H_7$ | sec sec $4H_9$ | 269–270 |
| iso $C_3H_7$ | iso $C_4H_9$ | 207–208 |
| iso $C_3H_7$ | n $C_3H_7$ | 107–108 |
| iso $C_4H_9$ | n $C_3H_7$ | 174–176 |
| iso $C_3H_7$ | neo $C_5H_{11}$ | 279–280 |
| t $C_4H_9$ | n $C_3H_7$ | 173–175 |
| sec butyl | neo $C_5H_{11}$ | 291–293 |
| t-$C_4H_9$ | neo $C_5H_{11}$ | 212–213 |

EXAMPLE 8

This Example illustrates the herbicidal effects of compounds 11 and 12 of Table I. A test was carried out as described in Example 1, but using an application rate of 1 kilogram per hectare for each compound. The results are given below in Table XV in terms of a 0 to 10 scale in which 0 is 0 to 9% damage, 9 is 90 to 99% damage and 10 is complete kill.

TABLE XV

| COMPOUND NO | PRE-EMERGENCE | | | | | POST-EMERGENCE | | | | |
|---|---|---|---|---|---|---|---|---|---|---|
| | Lt | To | Ot | Dg | Ll | Lt | To | Sb | Av | Dg | Ll |
| 11 | 1 | 1 | 3 | 3 | 8 | 0 | 0 | 0 | 10 | 8 | 9 |

TABLE XV-continued

| COM- POUND NO | PRE-EMERGENCE | | | | | POST-EMERGENCE | | | | |
|---|---|---|---|---|---|---|---|---|---|---|
| | Lt | To | Ot | Dg | Ll | Lt | To | Sb | Av | Dg | Ll |
| 12 | 1 | 1 | 9 | 9 | 9 | 0 | 0 | 1 | 10 | 10 | 10 |

The abbreviation Ll stands for *Lolium sp.*

The abbreviation Ll stands for *Lolium sp.*

EXAMPLE 9

This Example illustrates the herbicidal properties of a compound of the invention when applied in admixture with paraquat. In a glass-house test, well established (10 weeks old; grown from rhizome segments) pot-grown plants of the species *Agropyron repens* were sprayed with a composition comprising a finely divided suspension of compound no. 6 of Table I in a solution of paraquat dichloride. The spray volume corresponded to a rate of 1000 liters per hectare and the solution contained 0.1% by volume of "Agral" 90, a surface-active agent comprising a condensate of one molar proportion of p-nonyl phenol with from 7 to 8 molar proportions of ethylene oxide. Six weeks after spraying, the amount of regrowth from the underground rhizomes of the plants was assessed. Control of re-growth was expressed on a scale of 0 to 9 where 9 is complete suppression of re-growth. For comparison, compound no. 6 and paraquat were also applied separately.

TABLE XVI

| Treatment (Kg/Ha) | Control Of Regrowth (A) | Calculated Control Or Regrowth (E*) | Synergism (A-E) |
|---|---|---|---|
| Compound no. 6 (2) | 0 | — | — |
| Paraquat (1) | 5 | — | — |
| Compound no. 6 (2) + paraquat (1) | 9 | 5 | 4 |

*The value of E is calculated from the expression $$E = \frac{a + (100 - a)b}{100}$$

where a and b are the effects of compound no. 6 and paraquat in controlling regrowth when applied on their own. It may be noted that when using compound no. 6 on its own, an application rate of 4 kg/hectare was required to achieve complete suppression of regrowth (i.e. a score of 9).

It will be seen from Table XVI that the control of regrowth achieved when compound no. 6 was used in admixture with paraquat was greater than the expected effect (E) calculated on the basis of the herbicidal effect of each component when applied on its own. The mixture therefore showed a synergistic effect. Similar synergistic effects were observed with sequential applications, in which compound no. 6 was applied followed by paraquat at an interval of one, three, or seven days later.

In a further test carried out in Malaya, field plots of the plant species *Paspalum conjugatum* 6 meters by 2 meters in size were sprayed with compound no. 6 and with paraquat dichloride, in combination and separately. The spray volume was 400 liters per hectare, and the spray contained 0.1% Agral 90 as before. The damage to the plants was assessed 21 days later in terms of percentage scorch. The results are given in Table XVII below:

TABLE XVII

| Treatment KG/HA | Percentage Scorch | Calculated Scorch (E) | Synergism (A-E) |
|---|---|---|---|
| Paraquat (0.25) | 40 | — | — |
| Paraquat (0.5) | 50 | — | — |
| Compound no. 6 (4.0) | 55 | — | — |
| Compound no. 6 (4.0) + Paraquat (0.25) | 95 | 73 | 22 |
| Compound no. 6 (4.0) + Paraquat (0.5) + Compound no. 6 (4.0) | 95 | 78 | 17 |

It will be seen that the mixture treatments gave a greater degree of damage than would have been expected by calculation from the amount of damage caused by the components of the mixture applied separately; i.e. a synergistic effect.

EXAMPLE 10

This Example illustrates the herbicidal effect of compound no. 6 of Table I when applied in admixture with various additives. The compound was formulated for test as described in Example 2 and the additives then mixed in. The mixtures were sprayed on to 10 week old *Agropyron repens* plants grown in pots from rhizomes. After 6 weeks, the amount of regrowth from the underground rhizomes of the plants was assessed on a scale of 0 to 9 where 9 is complete suppression of regrowth and 0 is no suppression. The spray volume was 1000 liters per hectare. The results are given in Table XVIII below:

TABLE XVIII

| TREATMENT (KG/HA) | OBSERVED SUPPRESSION OR REGROWTH (A) | EXPECTED SUPPRESSION OF REGROWTH (E) | SYNERGISM (A-E) |
|---|---|---|---|
| Compound no. 6 (1) | 1 | — | — |
| TBP (1) | 1 | — | — |
| DMSO (50) | 1 | — | — |
| Compound no. 6 (1) + TBP (1) | 9 | 2 | 7 |
| Compound no. 6 (1) + DMSO (50) | 6 | 2 | 4 |
| Compound no. 6 (1) + (NH$_4$)$_2$SO$_4$ (10) | 9 | (1) | (8) |
| Compound no. 6 (10) + "Agral" 90 (1) | 9 | (1) | (8) |

The symbols TBP and DMSO stand for tributyl phosphate and dimethylsulphoxide respectively. The expected suppression of regrowth was calculated as in Example 9. The figures for expected suppression of regrowth and for synergism in the last two rows of the table are in brackets because no separate tests with ammonium sulphate and Agral 90 were performed. However, these substances would not be expected to cause phytotoxic damage since ammonium sulphate is used as a fertiliser and "Agral" 90 is a surfactant commonly used in pesticide sprays.

We claim:

1. A process of selectively controlling the growth of graminaceous weeds in a non-graminaceous crop, which comprises applying to the locus of said crop a triazine-dione compound of the formula:

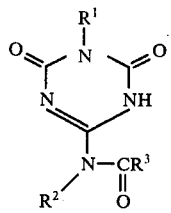

or a herbicidally effective salt thereof wherein $R^1$ is an alkyl radical of 3 to 5 carbon atoms in which the carbon atom attached to the ring nitrogen atom is a secondary or tertiary carbon atom; $R^2$ is an alkyl radical of from 3 to 5 carbon atoms, the alkyl radical being such that no carbon atom of the radical is linked through a linear sequence of more than two carbon atoms to the nitrogen atom to which $R^2$ is attached; and $R^3$ is a methyl, ethyl or cyclopropyl group, the amount of the triazine-dione compound applied being sufficient to control the growth of the graminaceous weeds, but insufficient to substantially damage the crop.

2. A process according to claim 1 wherein the triazine-dione compound is applied to the locus of said crop after the emergence of the crop.

3. A process as claimed in claim 1 wherein the rate of application of the triazine-dione compound is from 0.25 to 10 kilograms per hectare.

4. A process according to claim 1 wherein the crop is a leguminous crop.

5. A process according to claim 1 wherein the triazine-dione compound is one in which $R^1$ is an isopropyl group, $R^2$ is a neopentyl group, and $R^3$ is a methyl group.

6. A process according to claim 1 wherein the triazine-dione compound is one in which $R^1$ is a 2-butyl group, $R^2$ is a neopentyl group, and $R^3$ is a methyl group.

* * * * *